(12) United States Patent
Kim (10) Patent No.: US 9,532,855 B2
(45) Date of Patent: Jan. 3, 2017

(54) FUNCTIONAL IMPLANT

(71) Applicant: HIGH DENTAL KOREA CO., LTD., Seoul (KR)

(72) Inventor: Yong Hyeop Kim, Seoul (KR)

(73) Assignee: HANJIN DENTAL CO., LTD., Seoul (KR)

( * ) Notice: Subject to any disclaimer, the term of this patent is extended or adjusted under 35 U.S.C. 154(b) by 15 days.

(21) Appl. No.: 14/437,130

(22) PCT Filed: Jun. 3, 2013

(86) PCT No.: PCT/KR2013/004887
§ 371 (c)(1),
(2) Date: Apr. 20, 2015

(87) PCT Pub. No.: WO2014/061890
PCT Pub. Date: Apr. 24, 2014

(65) Prior Publication Data
US 2015/0272709 A1     Oct. 1, 2015

(30) Foreign Application Priority Data

Oct. 18, 2012  (KR) .................. 10-2012-0115681

(51) Int. Cl.
*A61C 5/10*  (2006.01)
*A61C 5/08*  (2006.01)
(Continued)

(52) U.S. Cl.
CPC .............. *A61C 8/0066* (2013.01); *A61C 5/08* (2013.01); *A61C 5/10* (2013.01); *A61C 8/0013* (2013.01);
(Continued)

(58) Field of Classification Search
CPC ............... A61C 5/10; A61C 5/08; A61C 8/00; A61C 13/09; A61C 8/066; A61C 8/0013; A61C 8/0048; A61C 8/0022; A61C 8/0068; A61C 8/0086
(Continued)

(56) References Cited

U.S. PATENT DOCUMENTS 6,648,645 B1 * 11/2003 MacDougald ......... A61C 5/002
                                              433/212.1
6,881,488 B2 *  4/2005 Giordano ........... A61C 13/0003
                                              428/426
(Continued)

FOREIGN PATENT DOCUMENTS

JP    2010-115304 A    5/2010
KR    10-0799368 B1    1/2008
KR    10-2009-0041380 A    4/2009

OTHER PUBLICATIONS

Search Report and Written Opinion for International Application No. PCT/KR2013/004887.

*Primary Examiner* — Nicholas Lucchesi
(74) *Attorney, Agent, or Firm* — LRK Patent Law Firm (57) ABSTRACT

A functional implant includes: a fixture; an abutment coupled to the upper portion of the fixture using a bolt; and a crown coupled to the abutment coupled to the fixture, the crown having a crown body concave on top thereof, an abutment insertion recess formed inside the crown body to be open on the underside of the crown body, and a coupling guide portion formed on an inner peripheral wall of the abutment insertion recess and having a scratch surface formed on the surface of the inner peripheral wall, a silica layer bonded to the scratch surface, a zirconia primer layer coated onto the silica layer, and a resin bonded to the zirconia primer layer. The crown is detachably coupled to the abutment through press-fitting, thereby allowing easy (Continued)

detachment and smooth repair and correction. The crown is made using milling, thus reducing errors to ensure good fitness and passivity.

9 Claims, 5 Drawing Sheets

(51) Int. Cl.
  *A61C 13/09*   (2006.01)
  *A61C 8/00*   (2006.01)
  *A61K 6/08*   (2006.01)

(52) U.S. Cl.
  CPC ........... *A61C 8/0022* (2013.01); *A61C 8/0048* (2013.01); *A61C 8/0068* (2013.01); *A61C 8/0086* (2013.01); *A61K 6/08* (2013.01)

(58) Field of Classification Search
  USPC ......... 433/173, 174, 175, 176, 202.1, 212.1, 433/218, 219, 222.1
  See application file for complete search history.

(56) References Cited

U.S. PATENT DOCUMENTS

| | | | |
|---|---|---|---|
| 8,834,161 B2* | 9/2014 | Vult Von Steyern | A61C 13/081 264/681 |
| 2004/0121291 A1 | 6/2004 | Knapp et al. | |
| 2008/0274440 A1* | 11/2008 | Smith | A61C 8/005 433/174 |
| 2009/0215010 A1* | 8/2009 | Tagami | A61C 13/0024 433/223 |
| 2012/0202170 A1* | 8/2012 | Johnson | A61C 8/005 433/173 |
| 2013/0130203 A1* | 5/2013 | Velamakanni | A61C 5/08 433/222.1 |

* cited by examiner

FUNCTIONAL IMPLANT

TECHNICAL FIELD

The present invention relates to a functional implant, and more particularly, to a functional implant that is provided with a crown having an abutment insertion recess formed inside a crown body and a coupling guide portion formed on an inner peripheral wall of the abutment insertion recess through the sequential application of a scratch surface, a silica layer, a zirconia primer layer, and a resin to the inner peripheral wall of the abutment insertion recess, so that the crown is detachably coupled to an abutment.

BACKGROUND ART

Generally, an implant is an artificial tooth root made of a material having no rejection reaction to the human body, which is placed into an alveolar bone from which a tooth is missing to replace the root of the missing tooth therewith, and after the artificial tooth root is integral into the alveolar bone, an artificial tooth is fixed to the artificial tooth root through a connection post, thus restoring the original function of the missing tooth.

An implant surgery is performed with an artificial tooth root that is integral into an alveolar bone from which a tooth is missing, a connection post that is accommodated into the artificial tooth root at one end thereof in such a manner that their parts are engaged with those of the artificial tooth root to prevent the rotation thereof, a screw that is accommodated into the interior of the connection post and coupled to the artificial tooth root, and an artificial tooth that is fastened to the front end periphery of the connection post.

The connection post for supporting the artificial tooth has an inclined surface formed on the portion accommodated into the artificial tooth root in such a manner as to be tightly engaged and fastened with the artificial tooth root by means of the screw, and accordingly, even if the screw is separated from the artificial tooth root so as to exchange the artificial tooth, the inclined surface of the connection post tightly engaged with the artificial tooth root is not easily removed from the artificial tooth root, thus delaying the surgery time due to the consumption of lots of time for the separation of the connection post.

If the connection post is not easily separated from the artificial tooth root, it should pull out by means of a tool like pliers, but in this case, shocks may be applied to adjacent teeth, thus causing additional teeth damages.

So as to allow the connection post to be fastened to the artificial tooth root, further, the screw should be inserted into the connection post to perform the fastening, which makes it very inconvenient in performing the implant surgery and causing the escape or loss of the screw at the time when the connection post is separated.

The artificial tooth is obtained by the following procedure. First, a plaster model made with an impression is cut through pin-work, and a wax model is made to have the shape and size of an artificial tooth to be molded through a wax-up. Next, if an investment surrounding the wax model is cured, the wax model is physically removed from the investment to form a mold frame, and a solution is poured into the mold frame to cast the artificial tooth. Finally, oxides formed on the surface of the cast artificial tooth are removed through polishing.

The artificial tooth made through the above-mentioned procedure is fixed to the connection post by means of screw-fastening or cementing.

In case where the impression is made in a patient's oral cavity, however, it is hard to make a real impression. Accordingly, errors may be generated in making the impression, which will sequentially occur in the model making, pin-work, wax-up, investment, casting and polishing, thus failing to ensure the fitness and passivity of the artificial tooth to cause the artificial tooth to be escaped after the implant surgery.

Since the artificial tooth is cast with the complicated procedure, further, a long period of time is needed until the implant surgery is completely finished, which gives many inconveniences to the patient.

Furthermore, the artificial tooth is coupled to the connection post by means of screw-fastening or cementing. In case of the screw-fastening, the screw may become loose or broken by means of lateral force and occlusal force (vertical pressure, lateral pressure and rotary pressure) applied to the artificial tooth when chewing operations are repeatedly conducted after the implant surgery, and in case of cementing, it is not easy to perform repair and correction of the artificial tooth and to conduct transition with which the implant is extended to adjacent teeth.

DISCLOSURE

Technical Problem

Accordingly, the present invention has been made in view of the above-mentioned problems occurring in the prior art, and it is an object of the present invention to provide a functional implant that has a crown detachably coupled to an abutment by means of press-fitting, thus allowing the crown to be easily separated from the abutment for the repair and correction and reducing the shocks applied to adjacent teeth, when separated, to prevent additional teeth damages, and that has the crown made through milling, thus reducing errors to ensure good fitness and passivity and preventing the crown from being separated from the abutment after surgery to extend the life span of the crown.

Technical Solution

To accomplish the above-mentioned object, according to the present invention, there is provided a functional implant including: a fixture; an abutment coupled to the upper portion of the fixture by means of a bolt; and a crown coupled to the abutment coupled to the fixture, the crown having a crown body concave on top thereof, an abutment insertion recess formed inside the crown body in such a manner as to be open on the underside of the crown body, and a coupling guide portion formed on an inner peripheral wall of the abutment insertion recess and having a scratch surface formed on the surface of the inner peripheral wall, a silica layer bonded to the scratch surface, a zirconia primer layer coated onto the silica layer, and a resin bonded to the zirconia primer layer.

According to the present invention, preferably, the abutment insertion recess having the coupling guide portion includes a shock-absorbing portion formed on the upper portion thereof, and the shock-absorbing portion has an upper inclined surface formed inclinedly downward toward the center thereof and a space portion formed on the underside of the upper inclined surface.

According to the present invention, preferably, the space portion of the shock-absorbing portion has a height in the range of 0.03 to 0.05 mm.

According to the present invention, preferably, the abutment insertion recess having the coupling guide portion has the shape of an elongated hole.

According to the present invention, preferably, the shock-absorbing portion of the abutment insertion recess includes a reinforcing portion formed on the other side of the upper inclined surface in such a manner as to be inclined downward toward the outside.

According to the present invention, preferably, the abutment insertion recess having the coupling guide portion includes a locking projection formed from the outer periphery of the inlet thereof, and the locking projection has a horizontal locking portion formed outward from the outer periphery of the inlet of the abutment insertion recess and an inclined locking portion inclinedly extended downward and outward from the outer periphery of the horizontal locking portion.

According to the present invention, preferably, the abutment includes an abutment body having a stepped hole vertically penetrated thereinto, a lower inclined surface formed on the top of the abutment body in such a manner as to have the same shape as the upper inclined surface of the shock-absorbing portion formed on the abutment insertion recess, a support projection formed along the lower periphery of the abutment body in such a manner as to be locked onto the locking projection formed on the lower periphery of the abutment insertion recess, and a tapered fixture insertion piece formed unitarily with the lower periphery of the abutment body.

According to the present invention, preferably, the fixture includes a fixture body having the shape of a cylinder whose lower portion is tapered and screw threads formed along the outer periphery thereof, a tapered groove formed on the upper portion of the fixture body, and a female screw formed on the center of the tapered groove.

Advantageous Effects

According to the present invention, the functional implant has the crown having the abutment insertion recess formed inside the crown body and the coupling guide portion formed on the inner peripheral wall of the abutment insertion recess through the sequential application of the scratch surface, the silica layer, the zirconia primer layer, and the resin to the inner peripheral wall of the abutment insertion recess, so that the crown is detachably coupled to the abutment by means of press-fitting, not by means of screw-fastening or cementing, thus allowing the crown to be easily separated from the abutment for the repair and correction.

Further, the functional implant according to the present invention has the crown easily separable from the abutment, thus reducing the shocks applied to adjacent teeth, when separated, to prevent additional teeth damages.

Furthermore, the functional implant according to the present invention has the crown made through milling, not through casting, thus reducing errors to ensure good fitness and passivity.

Additionally, the functional implant according to the present invention has the crown having good fitness and passivity, thus preventing the crown from being separated from the abutment after surgery to extend the life span of the crown.

BEST MODE FOR INVENTION

Hereinafter, an explanation on a functional implant according to the present invention will be in detail given with reference to the attached drawings.

Figure 1:
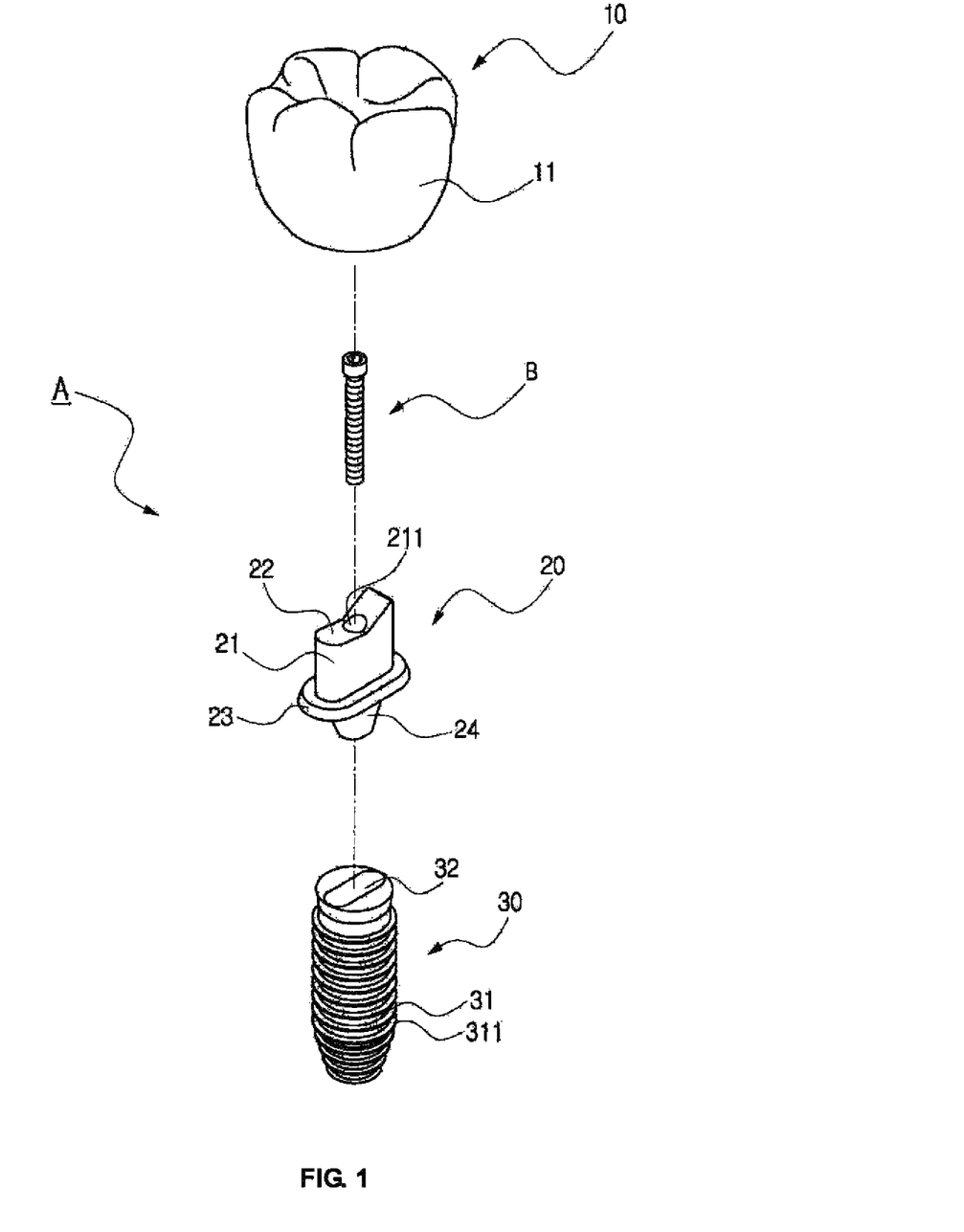
FIG. 1 is an exploded perspective view showing a functional implant according to the present invention.
Figure 2:
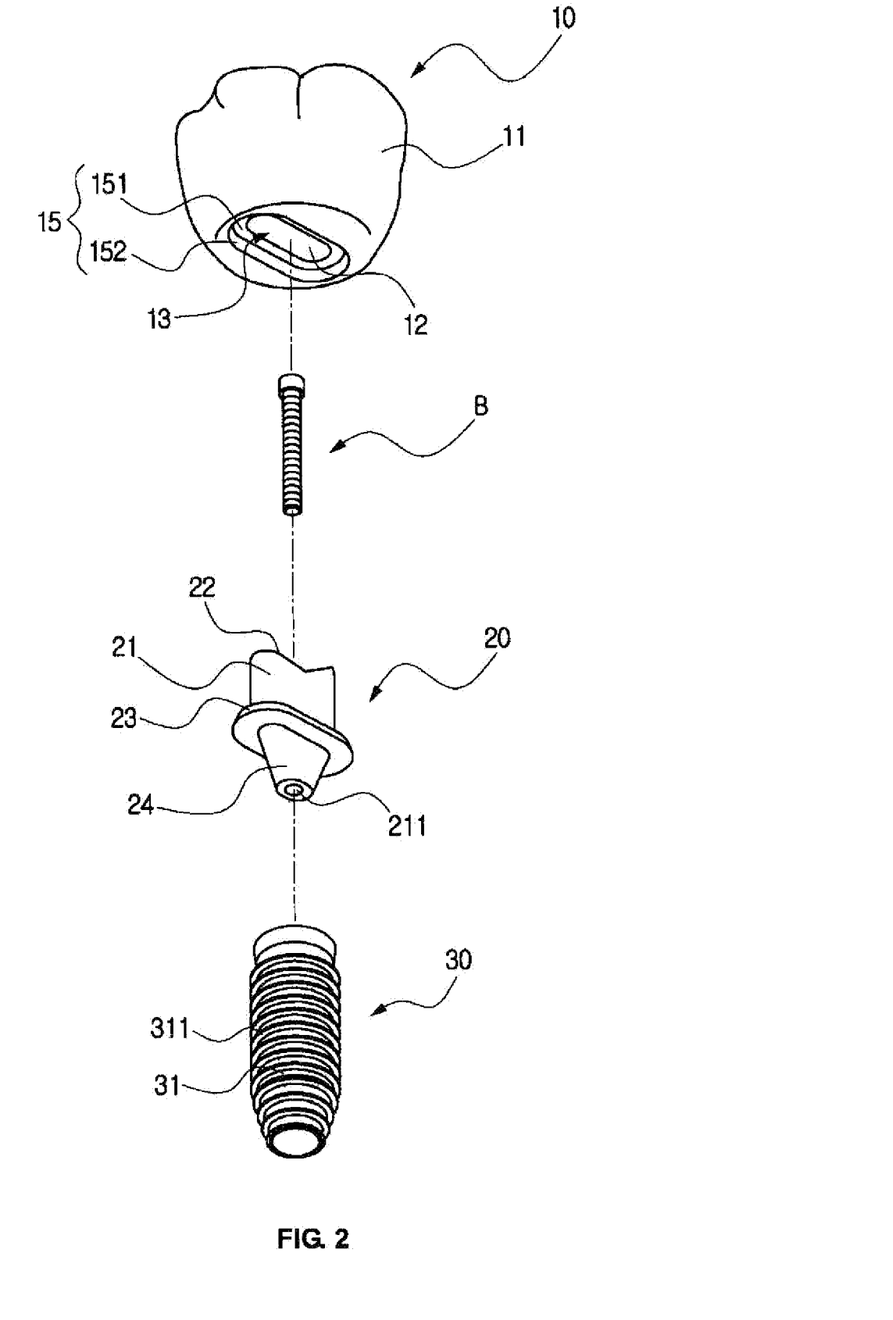
FIG. 2 is an exploded bottom perspective view showing the functional implant according to the present invention.
Figure 3:
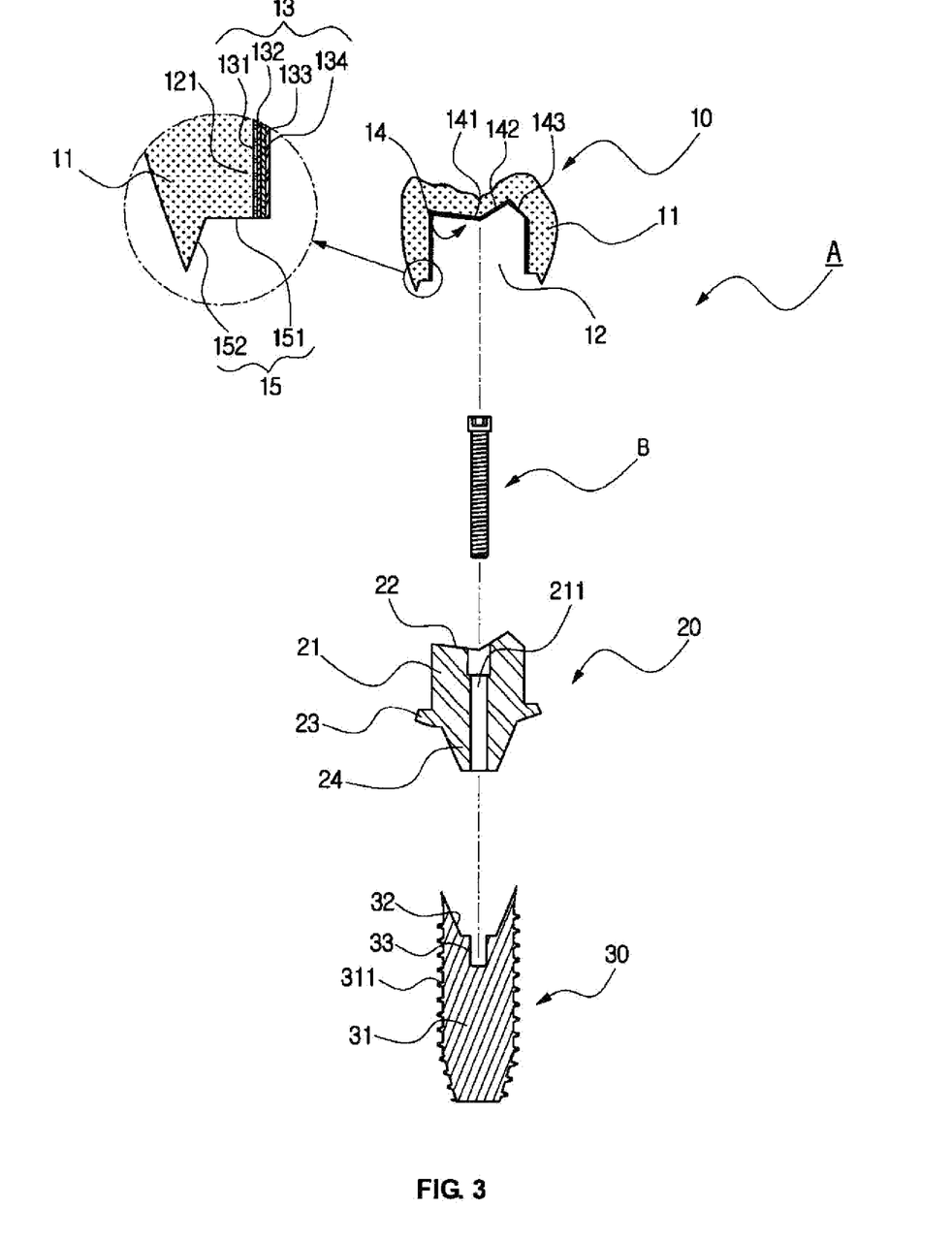
FIG. 3 is an exploded longitudinal sectional view showing the functional implant according to the present invention.
Figure 4:
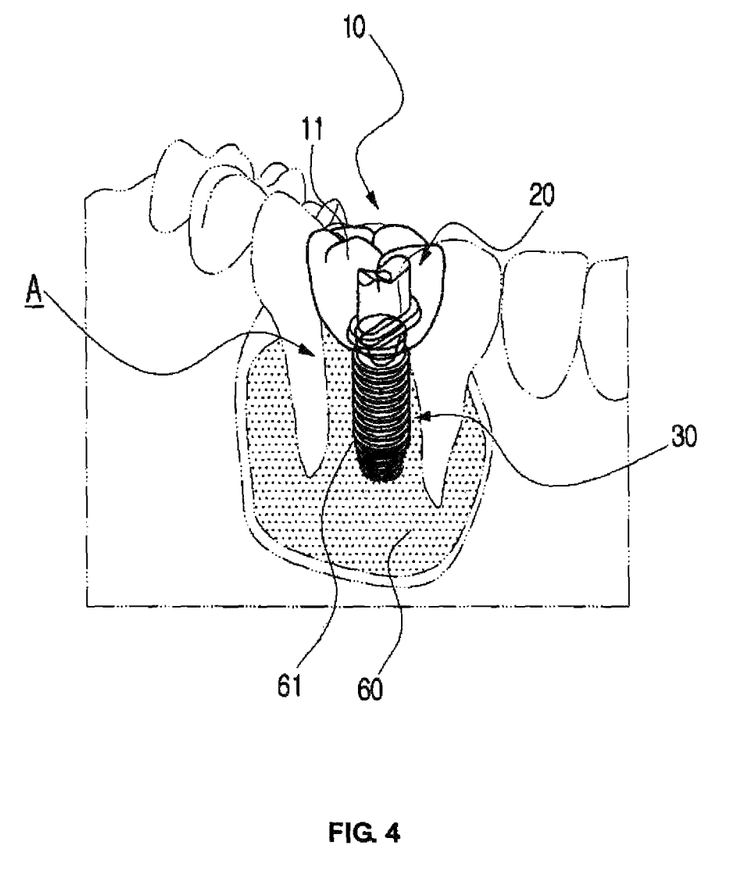
FIG. 4 is a perspective view showing the incised state of the functional implant after surgery.
Figure 5:
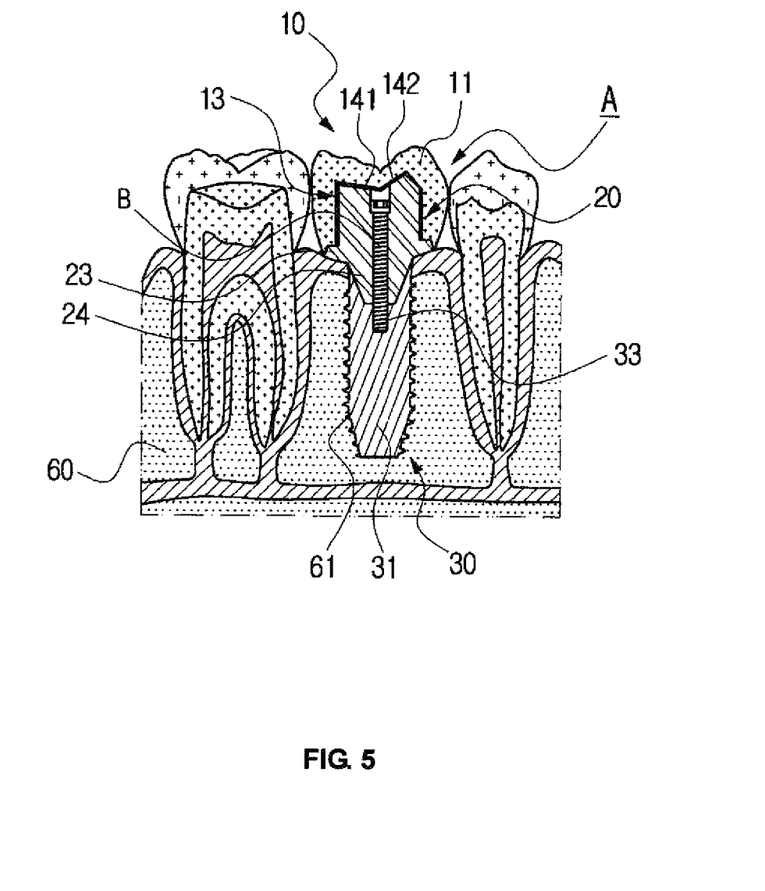
FIG. 5 is a longitudinal sectional view showing the functional implant after surgery.

As shown in FIGS. 1 to 5, a functional implant A according to the present invention includes a fixture 30 screw-coupled to a tooth extraction hole 61 formed on an alveolar bone 60, an abutment 20 coupled to the fixture 30 by means of a bolt B in such a manner as to allow the lower portion thereof to be fitted to the upper portion of the fixture 30, and a crown 10 detachably coupled to the abutment 20 coupled to the fixture 30 by means of the bolt B.

In this case, the crown 10 is formed by means of milling so as to have the same shape as the existing tooth and has a crown body 11 and an abutment insertion recess 12 formed inside the crown body 11 in such a manner as to be open on the underside of the crown body 11.

The crown 10 is made of zirconium dioxide ZrO2 and concave on the center of the upper portion thereof. The abutment insertion recess 12 is adapted to fit an abutment body 21 as will be discussed later thereto, thus preventing the crown 10 from moving in an arbitrary direction and absorbing the force applied from the upper portion of the crown 10, that is, the shocks occurring when food is chewed. Moreover, the abutment insertion recess 12 is easily detached from the abutment body 21 by means of a remover, thus easily conducting the repair, correction, and cleaning for the crown 10.

Accordingly, the abutment insertion recess 12 of the crown 10 has a coupling guide portion 13 having a given thickness formed on an inner peripheral wall 121 thereof.

The coupling guide portion 13 is configured to have a scratch surface 131 formed on the surface of the inner peripheral wall 121, a silica layer 132 bonded to the scratch surface 131, a zirconia primer layer 133 coated onto the silica layer 132, and a resin 134 bonded to the zirconia primer layer 133.

The scratch surface 131 serves to enhance a bonding force in the process where the silica layer 132 is bonded and is formed by means of sand scriptures. Desirably, the scratch surface 131 is formed with sand scriptures having the sizes of about 110 microns.

The silica layer 132 is formed in such a manner that silane powder is mixed with propane gas and the mixture is coated on the scratch surface 131, while being melted by means of flames of silica.

The zirconia primer layer 133 serves to enhance the bonding rate of the resin 134 bonded to the surface of the silica layer 132.

The resin 134 contains urethane and feldspar therein and does not cause any shrinkage or expansion therefrom, thus preventing the movements occurring in the state where the crown 10 is coupled to the abutment body 21 and avoiding the permeation of water into the coupled portion.

An angled surface (that is, occlusal surface) of the abutment insertion recess 12 is cut to have an angle of 2° and a thickness of 1 to 1.5 mm by means of milling, and the inner peripheral wall 121 is cut to have an angle of 0° by means of milling.

The abutment insertion recess 12 having the coupling guide portion 13 formed on the inner peripheral wall 121 thereof includes a shock-absorbing portion 14 formed as an occlusal surface on the upper portion thereof, and the shock-absorbing portion 14 has an upper inclined surface 141 formed inclinedly downward toward the center thereof and a space portion 142 formed on the underside of the upper inclined surface 141. The space portion 142 of the shock-absorbing portion 14 has a height in the range of 0.03 to 0.05 mm in such a manner as to provide an air pressure in the range of about 30 to 50 μton. That is, the pressure generated when food is chewed is absorbed by the chamber type space portion 142 constituting the shock-absorbing portion 14.

The shock-absorbing portion 14 of the abutment insertion recess 12 further includes a reinforcing portion 143 formed on the other side of the upper inclined surface 141 in such a manner as to be inclined downward toward the outside, and the reinforcing portion 143 serves to resist the lateral pressure generated when food is chewed.

The abutment insertion recess 12 having the coupling guide portion 13 has the shape of an elongated hole, thus preventing the abutment 20 coupled thereto from moving in every direction.

On the other hand, the abutment insertion recess 12 having the coupling guide portion 13 further includes a locking projection 15 adapted to be locked onto a support projection 23 of the abutment body 21 as will be discussed later, thus preventing the crown 20 from moving downward over a given limit.

The locking projection 15 has a horizontal locking portion 151 formed outward from the outer periphery of the inlet of the abutment insertion recess 12 so as to prevent the crown 10 from moving downward and an inclined locking portion 152 inclinedly extended downward and outward from the outer periphery of the horizontal locking portion 151 so as to prevent the center of the crown 10 from being misaligned.

The abutment 20 serves to allow the crown 20 to be detachably coupled to the upper portion of the fixture 30, and the abutment 20 includes the abutment body 21 having a stepped hole 211 vertically penetrated thereinto and a lower inclined surface 22 formed on the top of the abutment body 21 in such a manner as to have the same shape as the upper inclined surface 141 of the shock-absorbing portion 14 formed on the abutment insertion recess 12.

The abutment 20 further includes the support projection 23 formed along the lower periphery of the abutment body 21 in such a manner as to be locked onto the locking projection 15 formed on the lower periphery of the abutment insertion recess 12.

Further, the abutment 20 includes a tapered fixture insertion piece 24 formed unitarily with the lower periphery of the abutment body 21 in such a manner as to be coupled to a tapered groove 32 formed on the fixture 30 as will be discussed later, while the center of the tapered fixture insertion piece 24 is being automatically located at the center of the tapered groove 32.

The fixture 30, which is inserted into the tooth extraction hole 61 formed on the alveolar bone 60, includes a fixture body 31 having the shape of a cylinder whose lower portion is tapered and screw threads 311 formed along the outer periphery of the fixture body 31.

The fixture 30 further includes the tapered groove 32 formed on the upper portion of the fixture body 31 in such a manner as to allow the fixture insertion piece 24 formed on the lower portion of the abutment body 21 to be easily seated or inserted thereinto.

The fixture 30 further includes a female screw 33 formed on the center of the tapered groove 32 in such a manner as to be screw-coupled to the bolt B penetratedly inserted into the stepped hole 211 formed on the abutment body 21, thus rigidly fixing the abutment 20 thereto.

Like this, the implant A is installed by coupling the fixture 30 to the tooth extraction hole 61 formed on the alveolar bone 60 by means of the screw threads 311 formed on the outer periphery of the fixture body 31 and by seating the fixture insertion piece 24 formed on the lower portion of the abutment body 21 of the abutment 20 onto the tapered groove 32. At this time, the fixture insertion piece 24 of the abutment 20 is inserted into the tapered groove 32 in the state where the center of the tapered fixture insertion piece 24 is automatically located at the center of the tapered groove 32 by means of the inclination of the tapered groove 32.

Next, the bolt B is passed through the stepped hole 211 and screw-coupled to the female screw 33 formed on the fixture body 31, thus finishing the coupling of the abutment 20 to the fixture 30.

After that, the abutment insertion recess 12 formed on the crown 10 is fitted to the abutment body 21 of the abutment 20, thus completing the surgery of the implant A.

On the other hand, if the implant A after the installation in the above-mentioned procedure is separated for repair, correction and cleaning, the crown 10 first pulls out in a vertical direction by means of a remover, so that the crown 10 is easily separated from the abutment 20. After the repair, correction and cleaning, the crown 10 is coupled again to the abutment 20.

While the present invention has been described with reference to the particular illustrative embodiments, it is not to be restricted by the embodiment but only by the appended claims. It is to be appreciated that those skilled in the art can change or modify the embodiments without departing from the scope and spirit of the present invention.

The invention claimed is:

1. A functional implant comprising:
    a fixture (30);
    an abutment (20) coupled to an upper portion of the fixture (30) by a bolt B; and
    a crown (10) coupled to the abutment (20) coupled to the fixture (30) and having a crown body (11) concave on top thereof, an abutment insertion recess (12) formed inside the crown body (11) in such a manner as to be open on the underside of the crown body (11), and a coupling guide portion (13) formed on an inner peripheral wall (121) of the abutment insertion recess (12) and having a scratch surface (131) formed on the surface of the inner peripheral wall (121), a silica layer (132) bonded to the scratch surface (131), a zirconia primer layer (133) coated onto the silica layer (132), and a resin (134) bonded to the zirconia primer layer (133).

2. The functional implant according to claim 1, wherein the abutment insertion recess (12) having the coupling guide portion (13) comprises a shock-absorbing portion (14) formed on an upper portion thereof, and the shock-absorbing portion (14) has an upper inclined surface (141) formed inclinedly downward toward the center thereof and a space portion (142) formed on the underside of the upper inclined surface (141).

3. The functional implant according to claim 2, wherein the space portion (142) of the shock-absorbing portion (14) has a height in the range of 0.03 to 0.05 mm.

4. The functional implant according to claim 2, wherein the shock-absorbing portion (14) of the abutment insertion recess (12) comprises a reinforcing portion (143) formed on the other side of the upper inclined surface (141) in such a manner as to be inclined downward toward outside of the shock-absorbing portion (14).

5. The functional implant according to claim 2, wherein the abutment (20) comprises an abutment body (21) having a stepped hole (211) vertically penetrated thereinto, a lower inclined surface (22) formed on the top of the abutment body (21) in such a manner as to have the same shape as the upper inclined surface (141) of the shock-absorbing portion (14) formed on the abutment insertion recess (12), a support projection (23) formed along the lower periphery of the abutment body (21) in such a manner as to be locked onto the locking projection (15) formed on the lower periphery of the abutment insertion recess (12), and a tapered fixture insertion piece (24) formed unitarily with the lower periphery of the abutment body (21).

6. The functional implant according to claim 2, wherein the abutment insertion recess (12) having the coupling guide portion (13) has the shape of an elongated hole.

7. The functional implant according to claim 1, wherein the abutment insertion recess (12) having the coupling guide portion (13) has the shape of an elongated hole.

8. The functional implant according to claim 1, wherein the abutment insertion recess (12) having the coupling guide portion (13) comprises a locking projection (15) formed from the outer periphery of an inlet thereof, and the locking projection (15) has a horizontal locking portion (151) formed outward from the outer periphery of the inlet of the abutment insertion recess (12) and an inclined locking portion (152) inclinedly extended downward and outward from the outer periphery of the horizontal locking portion (151).

9. The functional implant according to claim 1, wherein the fixture (30) comprises a fixture body (31) having the shape of a cylinder whose lower portion is tapered and screw threads (311) formed along the outer periphery thereof, a tapered groove (32) formed on the upper portion of the fixture body (31), and a female screw (33) formed on the center of the tapered groove (32).

\* \* \* \* \*